(12) United States Patent
Todd et al.

(10) Patent No.: US 8,815,217 B2
(45) Date of Patent: Aug. 26, 2014

(54) TOOTH-BLEACHING PREPARATIONS

(75) Inventors: Christopher Todd, Hillsborough (GB); Sylvia Trimble, Dormore (GB)

(73) Assignee: SMT Research Limited, County Down (GB)

( * ) Notice: Subject to any disclaimer, the term of this patent is extended or adjusted under 35 U.S.C. 154(b) by 690 days.

(21) Appl. No.: 12/733,798

(22) PCT Filed: Sep. 18, 2008

(86) PCT No.: PCT/GB2008/050836
§ 371 (c)(1),
(2), (4) Date: Jul. 20, 2010

(87) PCT Pub. No.: WO2009/037505
PCT Pub. Date: Mar. 26, 2009

(65) Prior Publication Data
US 2011/0002860 A1    Jan. 6, 2011

(30) Foreign Application Priority Data

Sep. 20, 2007 (GB) .................................. 0718346.0

(51) Int. Cl.
| | | |
|---|---|---|
| *A61K 8/55* | (2006.01) | |
| *A61Q 11/02* | (2006.01) | |
| *A61K 8/42* | (2006.01) | |
| *A61K 8/22* | (2006.01) | |
| *A61Q 11/00* | (2006.01) | |
| *A61K 8/24* | (2006.01) | |

(52) U.S. Cl.
CPC . *A61Q 11/00* (2013.01); *A61K 8/42* (2013.01); *A61K 8/22* (2013.01); *A61K 8/24* (2013.01)
USPC .................... 424/57; 424/62; 424/53; 424/49

(58) Field of Classification Search
USPC ........................ 252/186.38; 424/53; 510/376
See application file for complete search history.

(56) References Cited

U.S. PATENT DOCUMENTS

| 5,648,064 A | 7/1997 | Gaffar et al. |
| 6,685,916 B1 | 2/2004 | Holme et al. |
| 2004/0202621 A1 | 10/2004 | Orlowski et al. |
| 2004/0241110 A1 | 12/2004 | Lee |

FOREIGN PATENT DOCUMENTS

| WO | WO03/024415 A2 | 3/2003 |
| WO | WO2006/098602 A1 | 9/2006 |

OTHER PUBLICATIONS

International Search Report issued May 5, 2009 in counterpart foreign application under the WIPO, Application No. PCT/GB2008/050836.
GB Search Report Under Section 17 issued Jan. 29, 2008 in GB priority Application No. GB0718346.0.

*Primary Examiner* — Walter Webb
(74) *Attorney, Agent, or Firm* — Michael Ye; Andrews Kurth LLP

(57) ABSTRACT

The present invention relates to a tooth bleaching preparation comprising an adduct formulated from starting materials comprising peroxide, urea and an alkali metal polyphosphate, the adduct being provided in the preparation in aqueous conditions and the preparation having a pH in aqueous solution which rises on dilution of the solution.

21 Claims, No Drawings

TOOTH-BLEACHING PREPARATIONS

This invention relates to tooth-bleaching preparations, and to certain chemical adducts useful in the formulation thereof.

It is well known in the art that hydrogen peroxide, carbamide peroxide (urea peroxide) and other peroxides can be used as bleaching agents in the formulation of tooth-bleaching gels. The prior art also discloses that carboxypolymethylene (Carbopol), poloxamer (Pluronic), and cellulosic gums, as well as other thickeners, can be used as the gelling agent in the preparation of peroxide gels.

Much attention has been paid in the art to controlling the pH of such compositions in use in order to optimize bleaching performance.

Thus, US2006251591 discloses dental compositions and methods for bleaching teeth directed towards hydrogen peroxide-containing compounds that are maintained at a substantially constant pH range of 6.0-10.0 during the tooth-bleaching procedure in the presence of a calcium chelating agent.

One difficulty that confronts the tooth-bleaching gel formulator, as acknowledged in US2006251591 is that hydrogen peroxide, in aqueous solution, is stable under acidic conditions but is a highly active bleaching agent under alkaline conditions.

Present ideas consider that hydrogen peroxide dissociates as a reversible reaction thus:

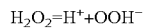

$$H_2O_2 = H^+ + OOH^-$$

and that it is the perhydroxyl (OOH$^-$) ion which is responsible for the bleaching effect. Since the reaction is reversible it will be shifted to the right if there is any alkali present to absorb the H$^+$ ions, i.e. if the pH value is relatively high. Under acid conditions there will be an abundance of hydrogen ions so the equilibrium will shift to the left and favour the stability of the less reactive hydrogen peroxide.

It would be desirable to produce an improved form of stable peroxide solution at a relatively high pH which can be used as a basis for a tooth-bleaching gel.

According to the present invention there is provided an adduct suitable for use in formulating a tooth-bleaching composition, the adduct being formulated from starting materials comprising peroxide, urea and an alkali metal polyphosphate, and having a pH in aqueous solution which rises on dilution of the solution.

The invention also concerns tooth bleaching preparations comprising the adduct, provided that such preparations are formulated with regard to the identity of any additional ingredients, and/or the relative proportions of those ingredients with respect to each other and/or with respect to the adduct to ensure that the tooth bleaching preparations of the invention also exhibit a pH in aqueous solution which rises upon dilution of the solution.

The inventors have found that by careful selection of the starting materials for the adduct, preferably with regard to their w/w % ratios relative to one another; by careful selection of any additional material, preferably with regard to its w/w % ratio relative to any other additional material and/or relative to the adduct; and/or by careful selection of the order or manner in which the ingredients are formulated, it is possible reliably to provide a tooth bleaching preparation which exhibits excellent tooth whitening properties and which has a pH in aqueous solution which rises on dilution (and hence in situ in the mouth when used) thereby, it is theorised, releasing additional active peroxide ions onto the teeth when used and providing thereby a superior performance with respect to certain prior art formulations which exhibit no such pH rise, or a significantly lower pH rise.

It is a surprising feature of the adduct or adduct combination, or of tooth bleaching preparations made therefrom, that the pH value of an aqueous solution of the adduct or combination or preparation appears to increase upon dilution to a significant extent. We have found that the pH of one adduct in accordance with the invention (the adduct described below in Example 1) in a 50% w/w aqueous solution to be approximately 7.5, and to increase to approximately 9.0 on dilution with water to 5% w/w.

Preferably the pH of the aforesaid solution at 50% w/w is above 7.0.

Preferably the pH of the aforesaid solution at 5% w/w is above 8.0.

We have found that certain prior art formulations may exhibit a modest pH rise on dilution, a characteristic which, it is believed, may be attributed to the presence, of Carbopol in such formulations. Although a modest pH rise upon dilution may have some beneficial effect in releasing peroxide ions when the formulation is used (ie deployed on the teeth) we believe that a more substantial pH rise on dilution is necessary or at least desirable in order to realise the superior performance of preparations in accordance with the invention. The chemical behaviour of the adduct in the preparations of the invention is believed to be largely, or at least significantly, responsible for the pH rise on dilution exhibited by the compositions and adducts of the invention.

Preferably the pH rise (of the tooth bleaching preparation and/or of the starting adduct solution) is at least about 0.1, preferably at least about 0.25, more preferably at least about 0.5, still more preferably at least about 1.0 and most preferably at least about 2.0 when diluted 2-fold or, alternatively, 5-fold or, alternatively, 10-fold. Such pH rises may be witnessed in the compositions of the invention even when formulated in the absence of Carbopol.

The peroxide and urea starting materials may be provided together as urea peroxide. Alternatively, other peroxides, preferably hydrogen peroxide, and urea may be provided as separate starting materials. Furthermore, the adducts of the invention may include three-component adducts in which a chemical combination of each of the starting materials is present; but also two-component adducts comprising a chemical combination of two of the starting materials provided that the two-component adduct is provided in contact or association with the third starting material, but importantly as or as part of an aqueous formulation having a pH which rises on dilution.

The preferred alkali metal polyphosphate is an alkali metal tripolyphosphate, in particular sodium tripolyphosphate.

Our experimental work has shown that the adduct of the invention, having the property of the pH rise in aqueous solution when diluted, is preferentially formulated with certain ratios of starting materials.

Preferably the ratio of alkali metal polyphosphate:peroxide in an aqueous solution of the adduct corresponds to an anhydrous alkali metal polyphosphate:hydrogen peroxide solution (35% w/w concentration) ratio by weight of from about 0.05:1 to about 0.5:1.

Preferably the ratio of alkali metal polyphosphate:urea in an aqueous solution of the adduct corresponds to an anhydrous alkali metal polyphosphate:urea ratio by weight of from about 0.1:1 to about 2.0:1.

Preferably the ratio of urea:peroxide in an aqueous solution of the adduct corresponds to a urea:hydrogen peroxide solution (35% w/w concentration) ratio by weight of from about 0.2:1 to about 1.0:1.

Also provided in accordance with the invention is a method for preparing an adduct suitable for use in formulating a tooth-bleaching composition, the method comprising providing the starting materials peroxide, urea and an alkali metal polyphosphate, and mixing the starting materials together in aqueous solution under conditions of temperature and/or pressure and/or agitation effective to provide a solution of the starting materials. The solution may then simply be combined with other desirable ingredients (if any) to provide a tooth bleaching formulation.

The invention also provides an adduct prepared in accordance with the aforesaid method, and a tooth bleaching formulation prepared in accordance with the method.

The invention also concerns the use of the adduct as aforesaid in the preparation of a tooth-bleaching formulation.

Also provided in accordance with the invention is a tooth-bleaching preparation comprising the aforesaid adduct or solution thereof.

The tooth-bleaching preparation in accordance with the above may comprise, in addition to the adduct, one or more further functional materials, excipients, carriers, thickeners, bleaching agents, stabilising agents and the like. The preparation may be formulated as a gel, solution, powder, dispersion, emulsion or the like, preferably as a gel.

The invention is further illustrated in the following Examples. All percentages are by weight and are expressed in terms of the total weight of the composition.

EXAMPLE 1

A peroxide/urea/polyphosphate adduct, which is suitable for use in formulating a tooth-bleaching gel, is produced from the ingredients set out below:

| Ingredient | % w/w |
| --- | --- |
| Hydrogen peroxide (35% soln.) | 55.0 |
| Sodium tripolyphosphate (anhydrous) | 18.0 |
| Urea | 27.0 |

We have found that there are a number of suitable ways to formulate the adduct, but one such method starts with the addition of the sodium tripolyphosphate to the hydrogen peroxide, followed by the urea. After the addition of the urea, the mixture is stirred until the urea is dissolved. The solution is then used to make a tooth-bleaching gel.

EXAMPLE 2

A tooth-bleaching gel was formulated from the adduct solution obtained in example 1 from the ingredients set out below:

| Ingredient | % w/w |
| --- | --- |
| Adduct | 36.0 |
| Glycerine | 36.0 |
| Polyvinylpyrrolidone | 25.0 |
| Deionised water to | 100.00 |

The ingredients were simply combined together to produce a tooth-bleaching gel in accordance with the invention.

EXAMPLE 3

A tooth-bleaching gel was formulated from the adduct solution obtained in example 1 from the ingredients set out below:

| Ingredient | % w/w |
| --- | --- |
| Adduct | 35.0 |
| Glycerine | 17.0 |
| Carbopol (polyacrylic acid) | 7.0 |
| Polyethylene glycol | 6.0 |
| Deionised water to | 100.00 |
| Sodium hydroxide (pH adjustor) | q.s. |

The ingredients were simply combined together to produce a tooth-bleaching gel in accordance with the invention.

EXAMPLE 4

A tooth bleaching gel was formulated directly from the ingredients set out below.

| Ingredient | % w/w |
| --- | --- |
| Urea | 1.60 |
| Sodium tripolyphosphate | 2.00 |
| Hydrogen peroxide 35% | 7.00 |
| Caustic soda | 7.50 |
| Carbopol 974 PNF | 8.00 |
| Glycerine | 36.45 |
| Minors (fragrance, sodium fluoride, etc.) | 0.90 |
| Deionised water to | 100 |

The method of mixing for this example is. Stage 1: the Carbopol, glycerine and the fragrance are blended together. Stage 2: the water, urea, sodium fluoride and other minor ingredients are blended until dissolved. Stage 3: stages 1 & 2 are mixed until homogeneous. Stage 4: caustic soda is added to stage 3 to neutralise the Carbopol. Stage 5: the hydrogen peroxide and STPP are blended and added to stage 4 and blended until homogeneous. The pH then is adjusted to c. 6.5.

The invention claimed is:

1. A tooth bleaching preparation, comprising an adduct formulated from starting materials comprising peroxide, urea and an alkali metal polyphosphate,
    wherein the ratio of alkali metal polyphosphate:peroxide in an aqueous solution of the adduct corresponds to an anhydrous alkali metal polyphosphate:hydrogen peroxide solution (35% w/w concentration) ratio by weight of from about 0.05:1 to about 0.5:1, the adduct being provided in the preparation in aqueous conditions and the preparation and/or the adduct having a pH in aqueous solution which rises by at least 1.0 on a 10-fold dilution of the solution.

2. A tooth bleaching preparation according to claim 1, wherein the pH rise is at least about 0.5 when diluted 5-fold.

3. A tooth bleaching preparation according to claim 2, wherein the pH rise is at least about 0.25 when diluted 2-fold.

4. A tooth bleaching preparation according to claim 1, wherein the pH of the solution at 50% w/w is above 7.0.

5. A tooth bleaching preparation according to claim 4, wherein the pH of the solution when diluted to 5% w/w is above 8.0.

6. A tooth bleaching preparation according to claim 1, wherein the peroxide and urea starting materials are provided together as urea peroxide.

7. A tooth bleaching preparation according to claim 1, wherein the peroxide and urea are provided as separate starting materials.

8. A tooth bleaching preparation according to claim 7 wherein the peroxide is hydrogen peroxide.

9. A tooth bleaching preparation according to claim 1, wherein the alkali metal polyphosphate is an alkali metal tripolyphosphate.

10. A tooth bleaching preparation according to claim 9 wherein the alkali metal tripolyphosphate is sodium tripolyphosphate.

11. A tooth bleaching preparation according to claim 1, wherein the ratio of alkali metal polyphosphate:urea corresponds to an anhydrous alkali metal polyphosphate:urea ratio by weight of from about 0.1:1 to about 2.0:1.

12. A tooth bleaching preparation according to claim 1, wherein the ratio of urea:peroxide corresponds to a urea: hydrogen peroxide solution (35% w/w concentration) ratio by weight of from about 0.2:1 to about 1.0:1.

13. A tooth-bleaching preparation according to claim 1, comprising one or more further functional materials, excipients, carriers, thickeners, bleaching agents and/or stabilising agents.

14. An adduct suitable for use in formulating a bleaching composition, the adduct being formulated from starting materials comprising peroxide, urea and an alkali metal polyphosphate, wherein the ratio of alkali metal polyphosphate:peroxide in an aqueous solution of the adduct corresponds to an anhydrous alkali metal polyphosphate:hydrogen peroxide solution (35% w/w concentration) ratio by weight of from about 0.05:1 to about 0.5:1, and the adduct having a pH in aqueous solution which rises by at least 1.0 on a 10-fold dilution of the solution.

15. The adduct of claim 14, wherein the ratio of alkali metal polyphosphate:urea corresponds to an anhydrous alkali metal polyphosphate:urea ratio by weight of from about 0.1:1 to about 2.0:1.

16. The adduct of claim 14, wherein the ratio of urea: peroxide corresponds to a urea:hydrogen peroxide solution (35% w/w concentration) ratio by weight of from about 0.2:1 to about 1.0:1.

17. The adduct of claim 14, wherein the alkali metal polyphosphate is an alkali metal tripolyphosphate.

18. A method for preparing an adduct of claim 1, comprising:
    providing starting materials; and
    mixing the starting materials together in aqueous solution under conditions of temperature and/or pressure and/or agitation effective to obtain a solution of the starting materials,
    wherein the starting materials comprise peroxide, urea and an alkali metal polyphosphate, wherein the alkali metal polyphosphate:peroxide ratio corresponds to an anhydrous alkali metal polyphosphate:hydrogen peroxide solution (35% w/w concentration) ratio by weight of from about 0.05:1 to about 0.5:1, and wherein the adduct has a pH in aqueous solution which rises by at least 1.0 on a 10-fold dilution of the solution.

19. The method of claim 17, wherein the ratio of alkali metal polyphosphate:urea corresponds to an anhydrous alkali metal polyphosphate:urea ratio by weight of from about 0.1:1 to about 2.0:1.

20. The adduct of claim 17, wherein the ratio of urea: peroxide corresponds to a urea:hydrogen peroxide solution (35% w/w concentration) ratio by weight of from about 0.2:1 to about 1.0:1.

21. A tooth bleaching preparation, comprising an adduct formulated from starting materials comprising peroxide, urea and an alkali metal polyphosphate,
    wherein the ratio of alkali metal polyphosphate:peroxide in an aqueous solution of the adduct corresponds to an anhydrous alkali metal polyphosphate:hydrogen peroxide solution (35% w/w concentration) ratio by weight of from about 0.05:1 to about 0.5:1, the ratio of alkali metal polyphosphate:urea corresponds to an anhydrous alkali metal polyphosphate:urea ratio by weight of from about 0.1:1 to about 2.0:1, and the ratio of urea:peroxide corresponds to a urea:hydrogen peroxide solution (35% w/w concentration) ratio by weight of from about 0.2:1 to about 1.0:1, the adduct being provided in the preparation in aqueous conditions and the preparation and/or the adduct having a pH in aqueous solution which rises by at least 1.0 on a 10-fold dilution of the solution.

* * * * *